United States Patent
Hanazaki et al.

(10) Patent No.: US 6,864,982 B2
(45) Date of Patent: Mar. 8, 2005

(54) GAS ANALYZING METHOD AND GAS ANALYZER FOR SEMICONDUCTOR TREATER

(75) Inventors: Minoru Hanazaki, Hyogo (JP); Toshiki Oono, Hyogo (JP)

(73) Assignees: Renesas Technology Corp., Tokyo (JP); Mitsubishi Electric Engineering Company Limited, Tokyo (JP)

( * ) Notice: Subject to any disclaimer, the term of this patent is extended or adjusted under 35 U.S.C. 154(b) by 9 days.

(21) Appl. No.: 10/162,882

(22) Filed: Jun. 6, 2002

(65) Prior Publication Data

US 2003/0046976 A1 Mar. 13, 2003

(30) Foreign Application Priority Data

Sep. 7, 2001 (JP) ........................................ 2001-271440

(51) Int. Cl.⁷ .............................................. G01N 21/00
(52) U.S. Cl. ....................................................... 356/437
(58) Field of Search .......................... 134/1.1; 356/437; 156/345

(56) References Cited

U.S. PATENT DOCUMENTS 6,146,492 A * 11/2000 Cho et al. .............. 156/345.24
6,493,086 B1 * 12/2002 McAndrew et al. ........ 356/437
6,499,492 B1 * 12/2002 Cho et al. ..................... 134/1.1

FOREIGN PATENT DOCUMENTS

| JP | 61-97928 | 5/1986 |
| JP | 2-82131 | 3/1990 |

* cited by examiner

*Primary Examiner*—John F. Niebling
*Assistant Examiner*—Andre' C. Stevenson
(74) *Attorney, Agent, or Firm*—McDermott Will & Emery LLP

(57) ABSTRACT

A gas analyzer for a semiconductor treater improved to be capable of monitoring leakage or change of gas composition influencing treatability of the semiconductor treater in situ is provided. A duct is provided on the outer wall of a chamber of the semiconductor treater for taking out gas to be analyzed from the chamber. A gas analytic chamber stores the gas to be analyzed taken out through the duct. A discharge formation part is mounted in the vicinity of the gas analytic chamber. The discharge formation part includes a high frequency generation coil generating a high frequency and forming a plasma of the gas to be analyzed in the gas analytic chamber. This gas analyzer further comprises a spectrometer analyzing the emission wavelength of the plasma of the gas to be analyzed.

6 Claims, 5 Drawing Sheets

GAS ANALYZING METHOD AND GAS ANALYZER FOR SEMICONDUCTOR TREATER

BACKGROUND OF THE INVENTION

1. Field of the Invention

The present invention generally relates to a gas analyzing method for a semiconductor treater, and more specifically, it relates to a gas analyzing method for a semiconductor treater so improved as to monitor leakage or change of gas composition influencing the treatability of the semiconductor treater employing a vacuum in situ for improving the productivity and the reliability of the semiconductor treater. The present invention also relates to a gas analyzer for a semiconductor treater capable of implementing such a method.

2. Description of the Background Art

A semiconductor treater is now described with reference to a plasma treater such as a dry etching apparatus (hereinafter referred to as an etching apparatus), for example, treating a semiconductor wafer (hereinafter referred to as a wafer) with a plasma.

The etching apparatus introduces treating gas into a plasma treatment chamber (hereinafter referred to as a chamber) set to a vacuum atmosphere for generating a plasma thereby forming chemically active ions and radicals (neutral active species) by ionization or dissociation of the treating gas. The ions and radicals physically or chemically act to etch a desired portion of a treated film provided on the wafer for forming a desired device pattern.

At this time, leakage to the outside air takes place in a vacuum sealing part of the chamber or a treating gas supply system, such that atmospheric components are mixed into the treating gas or the flow rate of the treating gas or the like is changed by some cause. In this case, the compositions of the ions and radicals contained in the plasma are so changed that no desired etching characteristic is attained but the reliability and the productivity of a semiconductor device are remarkably inhibited.

In general, therefore, pressure change is checked with a vacuum meter, emission of the plasma is analyzed, or a helium leak detector or a mass spectrometer is employed for analyzing the gas in the chamber.

However, in the method employing a vacuum meter, for example, it is difficult to sense slight leakage due to low sensitivity, although pressure increase resulting from leakage can be sensed. Further, this method is inferior in reliability due to change of the sensitivity of the vacuum meter caused by a reactive plasma or insufficient reproducibility. Further, it can be said substantially impossible to analyze the gas species in this method in principle.

Japanese Patent Laying-Open No. 02-82131 (1990) discloses a method of checking leakage with a helium leak detector. However, the measurer employed in this method is relatively high-priced although the same has high sensitivity. Further, He gas must be supplied around the chamber or the like, and an He gas spray must be mounted on a vacuum pumping system of the apparatus for making an inspection. In addition, this method cannot make measurement during etching, and cannot analyze gas species.

A mass spectrometer such as a quadruple mass spectrometer (Q-Mass) is capable of highly sensitive gas analysis, leakage check and in-situ monitoring during etching. However, the mass spectrometer is disadvantageously high-priced. Further, the sensitivity of the mass spectrometer is remarkably changed due to contamination of a measuring electrode or an ionization filament with a reaction product formed during etching, deterioration by an active plasma or the like, and only a qualitative result can be obtained. Further, metal contamination may be caused on the wafer with an electrode material.

Japanese Patent Laying-Open No. 61-97928 (1986) proposes a method of identifying gas species by analyzing radicals and ions contained in a plasma employed for treating a wafer through emission of the plasma. This method enables highly sensitive in-situ monitoring. Further, this method causes no influence such as metal contamination on the process due to optical observation through a window formed on a chamber wall. In addition, atmospheric leakage can be checked by detecting the emission spectrum (335 nm, 674 nm or the like) of nitrogen contained in the atmosphere. In this method, however, the emission strength is inevitably reduced by hazing of a measuring window provided on the chamber resulting from a reaction product formed during etching. Thus, periodic cleaning must be inevitably performed for preventing reduction of detection sensitivity. Further, the emission spectrum of nitrogen or oxygen employed for leakage check may frequently overlap with the emission spectrum of a treated plasma depending on the type of the treating gas, and it is difficult to apply this method to a recent etching apparatus employing various types of gas. Further, the gas analyzing method employing emission spectroscopy can be executed only during plasma generation (treatment) as a matter of course, and cannot be applied to an apparatus utilizing no plasma.

In addition, the species of gas having no emission spectrum data cannot be identified, as a matter of course. Even in gas having a known emission spectrum, the strength of the spectrum may change or overlap with the spectrum of another gas to cause difficulty in identification of the gas species depending on mixed gas or discharge conditions.

SUMMARY OF THE INVENTION

The present invention has been proposed in order to solve the aforementioned problems, and an object thereof is to provide a gas analyzing method for a semiconductor treater so improved as to employ no plasma in product treatment.

Another object of the present invention is to provide a gas analyzing method for a semiconductor treater also applicable to gas analysis of a non-plasma apparatus.

Still another object of the present invention is to provide a gas analyzing method for a semiconductor treater so improved as to cause no metal contamination.

A further object of the present invention is to provide a gas analyzing method for a semiconductor treater so improved as to enable precise in-situ gas analysis.

A further object of the present invention is to provide a gas analyzer capable of executing such a gas analyzing method for a semiconductor treater.

In a gas analyzer for a semiconductor treater according to a first aspect of the present invention, a duct for taking out gas from a chamber of the semiconductor treater is provided on the outer wall of the chamber. The gas analyzer comprises a gas analytic chamber storing the gas to be analyzed taken out through the aforementioned duct. A discharge formation part is mounted in the vicinity of the aforementioned gas analytic chamber. The aforementioned discharge formation part includes a high frequency generator generating a high frequency for forming a plasma of the aforementioned gas to be analyzed in the aforementioned gas analytic chamber.

The gas analyzer further comprises an analyzer for analyzing the emission wavelength of the plasma of the aforementioned gas to be analyzed.

In a gas analyzing method for a semiconductor treater according to a second aspect of the present invention, gas is first taken out from a chamber of a semiconductor treater. The aforementioned gas is stored in a gas analytic chamber. A high frequency is fed into the aforementioned gas analytic chamber from outside the gas analytic chamber for forming a plasma in the gas analytic chamber. The emission spectrum of the aforementioned plasma is analyzed.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Embodiments of the present invention are now described with reference to the drawings.

First Embodiment

Figure 1:
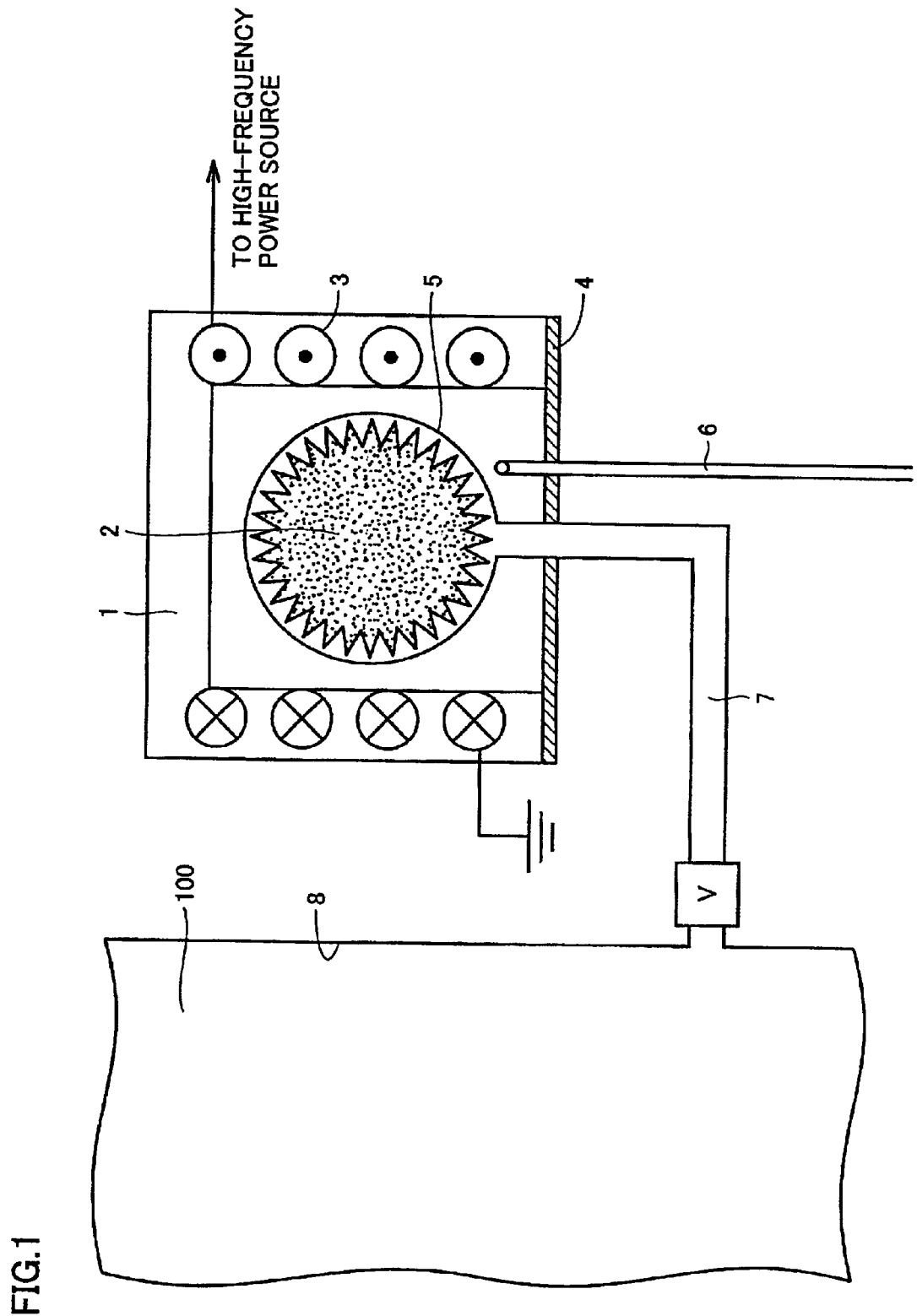
FIG. 1 is a conceptual diagram showing an exemplary in-situ gas analyzing method for a semiconductor treater according to a first embodiment of the present invention.

FIG. 1 is a conceptual diagram showing an exemplary in-situ gas analyzing method for a semiconductor treater according to a first embodiment of the present invention.

A gas analytic pipe 7 for taking out gas from a vacuum treatment chamber (hereinafter referred to as a chamber) 100 of the semiconductor treater is provided on part of an outer wall 8 of the chamber 100. A gas analytic discharge part 5 made of a transparent dielectric material such as quartz is mounted on the forward end of the gas analytic pipe 7. A detachable discharge formation part 1 is mounted around the gas analytic discharge part 5. The discharge formation part 1 includes a high-frequency coil 3 wound on the gas analytic discharge part 5. A high-frequency power source (not shown) supplies a high-frequency current to the high-frequency coil 3 so that gas contained in the gas analytic discharge part 5 discharges and an emission spectrometer (not shown) analyzes the emission wavelength of a plasma 2 formed by the gas through an emission analyzing fiber member 6.

A shield 4 is mounted in order to prevent leakage of high-frequency noise from the high-frequency coil 3 and block external light. The gas analytic pipe 7 has a labyrinth structure so bent that light of a plasma or the like formed by the semiconductor treater or a reaction product is not directly in contact with the gas analytic discharge part 5. A valve V is provided on an intermediate portion of the gas analytic pipe 7, for preventing the reaction product from penetrating into the gas analytic discharge part 5.

According to this structure, the gas contained in the chamber 100 of the semiconductor treater generates an inductively coupled plasma (ICP) through the high-frequency coil 3 wound on the outer periphery of the gas analytic discharge part 5. Thus, the gas guided from the semiconductor treater is dissociated and ionized in the plasma to emit light having a specific wavelength responsive to the components thereof. The components forming the gas can be analyzed by analyzing the emission wavelength of the light through a spectrometer.

According to this embodiment capable of analyzing the emission by the plasma without through the plasma in the semiconductor treater, gas analysis can be executed in situ not only during semiconductor treatment (plasma generation) but also at arbitrary timing.

Also in a semiconductor formation apparatus having no plasma generation means, gas analysis can be executed through plasma emission analysis in situ or at arbitrary timing, as a matter of course.

The gas analytic discharge part 5 may be provided with no electrode therein for generating the inductively coupled plasma. In this analysis, therefore, a possibility of metal contamination from the gas analyzer can be ignored. Further, the gas analytic discharge part 5 made of quartz is not deteriorated but capable of stable gas analysis over a long period.

Figure 2:
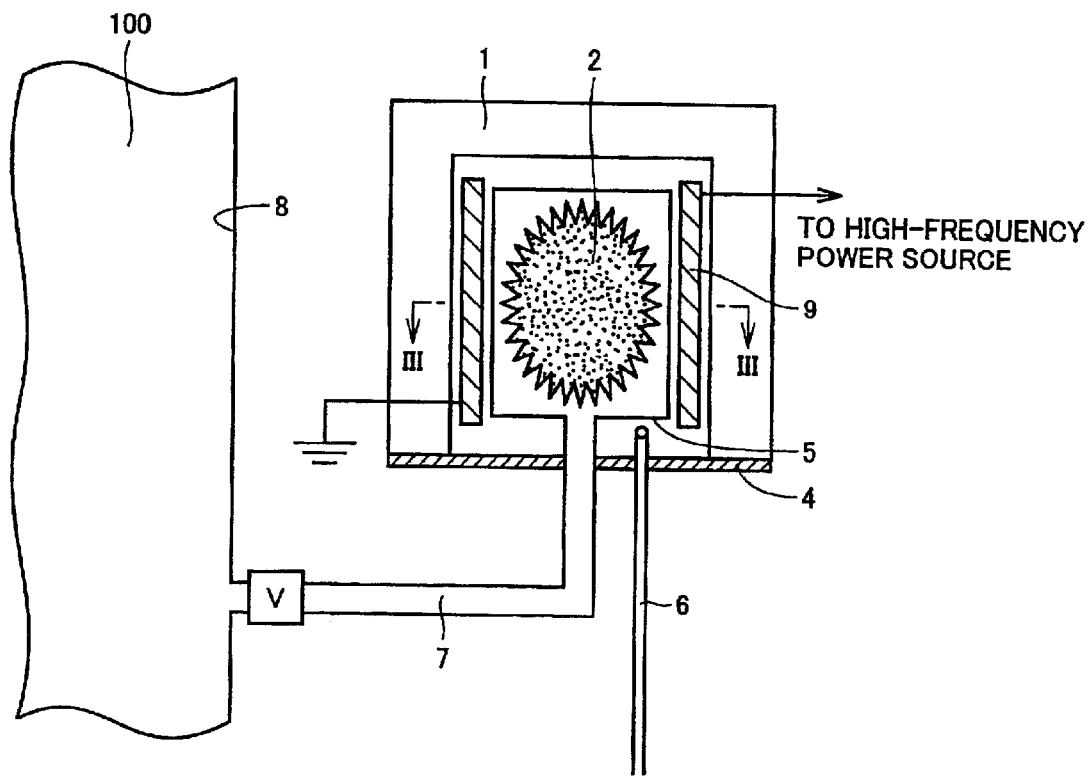
FIG. 2 is a conceptual diagram showing a gas analyzer according to another mode of the first embodiment.

Discharge can be formed in an electrodeless manner by a capacitively coupled plasma (CCP) system employing high-frequency electrodes 9 provided outside the gas analytic discharge part 5 for applying a high-frequency voltage as shown in FIG. 2 or by a discharge system employing microwaves. Referring to FIGS. 2 to 5, elements identical or corresponding to the members shown in FIG. 1 are denoted by the same reference numerals, and redundant description is not repeated.

A magnetic field (not shown) may be formed in the vicinity of the discharge part 5 by a permanent magnet or the like, in order to improve ignitability or stability of the discharge. When discharge means such as electron cyclotron resonance (ECR) discharge, for example, formed by combination of microwaves and a magnetic field is employed, the ignitability and the stability of the discharge can be further improved, as a matter of course.

Figure 3:
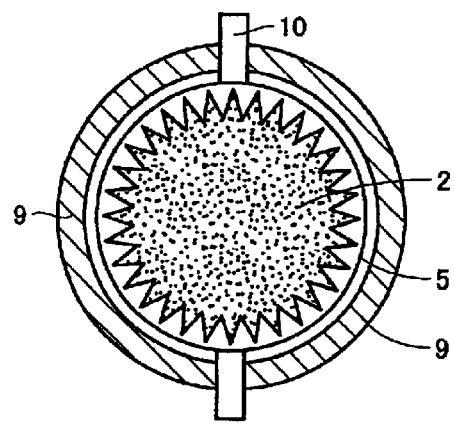
FIG. 3 is a sectional view taken along the line III—III in FIG. 2.

FIG. 3 shows a section taken along the line III—III in FIG. 2 as viewed from above, for illustrating the structures of the high-frequency electrodes 9 and the gas analytic discharge part 5. Two high-frequency electrodes 9 are opposed to each other about the gas analytic discharge part 5 through an insulator 10.

Referring again to FIG. 1, the gas analytic pipe 7 reaching the gas analytic discharge part 5 is bent substantially at a right angle for suppressing penetration of incident light or a reaction product from the semiconductor treater. This labyrinth structure is not restricted to the aforementioned one. The gas analytic pipe 7 may alternatively be bent as a structure blocking light. A plate for blocking light or the like may be provided in the pipe. Similarly, the aspect ratio (pipe length/pipe diameter) of the analytic pipe 7 may be enlarged or a filter may be introduced into an intermediate portion of the analytic pipe 7, in order to prevent penetration of the reaction product. During general treatment, the valve V is closed for preventing penetration of reactive gas.

While the gas analytic pipe 7 is provided on the outer wall 8 of the semiconductor treater in FIG. 1, any part can be employed so far as the same allows gas analysis in an intermediate portion of a pipe or the like.

Alternatively, gas analytic discharge parts 5 may be previously mounted on a plurality of portions. Detachable discharge formation parts 1 may be mounted on the gas analytic discharge parts 5 at need, for executing gas analysis.

Gas analysis of a number of semiconductor treaters can be performed by carrying the single gas analytic discharge part 5.

Second Embodiment

In the conventional method of performing gas analysis of a semiconductor treater by emission spectroscopy, gas species can be subjected to identification, i.e., qualitative analysis by making object gas emit light in a plasma and specifying the emission wavelength thereof. However, it is difficult to quantitatively analyze gas, since the quantity of emission from the plasma may be changed with time due to hazing of a photoreceiving window mounted on a wall of the semiconductor treater or it is difficult to calibrate reference emission.

Figure 4:
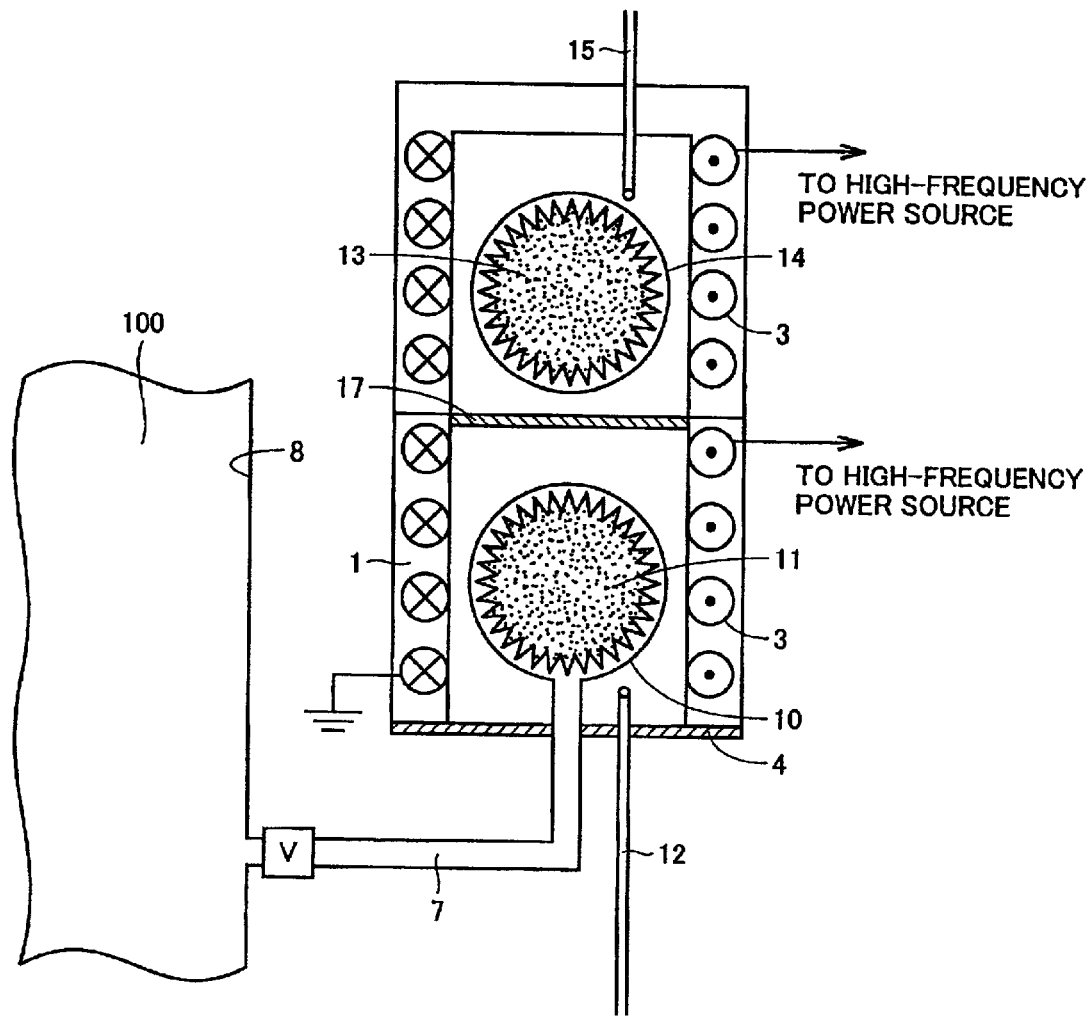
FIG. 4 is a conceptual diagram showing an analyzer according to a second embodiment of the present invention.

A second embodiment of the present invention enables quantitative gas analysis by employing a calibration discharge part previously filled with known gas. FIG. 4 is a conceptual diagram for illustrating a method according to the second embodiment.

Referring to FIG. 4, a calibration discharge part 14 of the same shape, the same material and the same thickness is provided in addition to an analyzing discharge part 10 performing emission spectrometry of gas from a semiconductor treater. According to the second embodiment, the discharge parts 10 and 14 are made of quartz. The calibration discharge part 14 is previously filled with gas of a previously defined type and a previously defined partial pressure. A screen 17 is provided between the analyzing discharge part 10 and the calibration discharge part 14, for separating the discharge parts 10 and 14 from each other. A high-frequency coil 3 provided in a discharge formation part 1 is wound by the same number of turns for the analyzing discharge part 10 and the calibration discharge part 14, and capable of supplying the same high-frequency power to the discharge parts 10 and 14. The discharge formation part 1 is dividable so that the calibration discharge part 14 can be exchanged.

Figure 5:
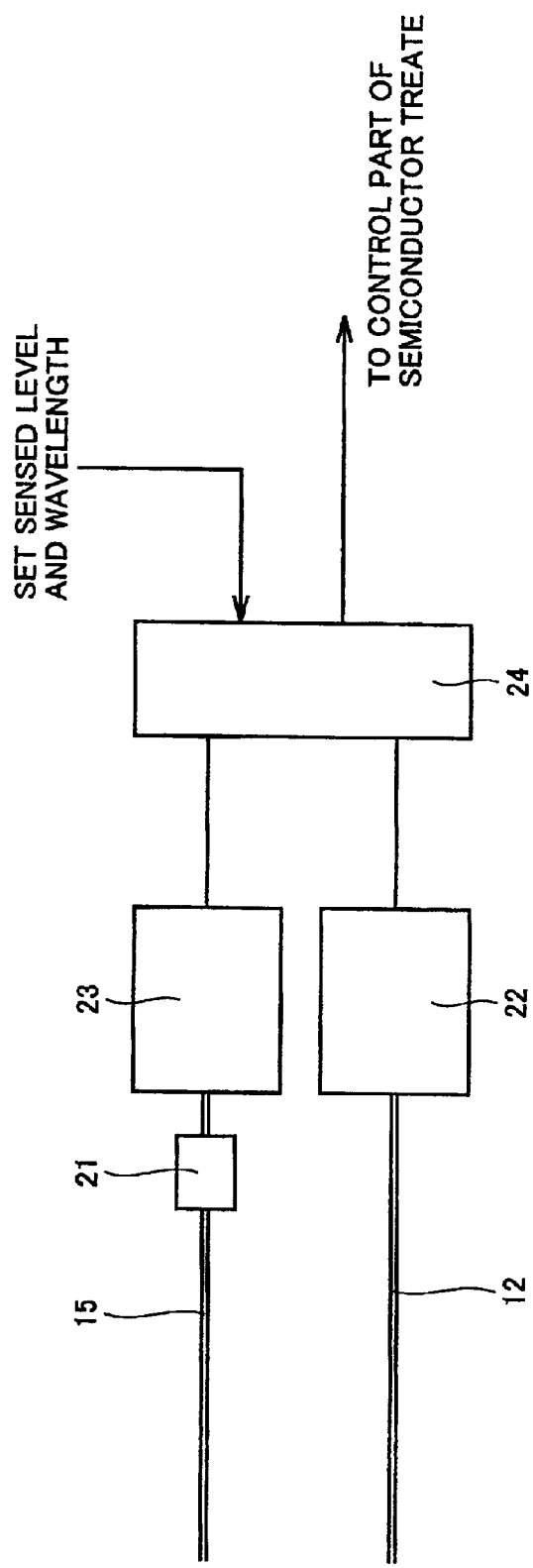
FIG. 5 is a conceptual diagram for illustrating a gas analyzing method according to the second embodiment.

The gas analyzing method according to the second embodiment is now described with reference to FIG. 5.

Light emitted from each plasma is guided to an analytical spectrometer 22 and a calibration spectrometer 23 through an analyzing optical fiber member 12 and a calibration optical fiber member 15 respectively. It is assumed that the materials for and the lengths of the fiber members 12 and 15 are basically identical to each other. However, an attenuator (diaphragm) 21 is provided on an end of the calibration optical fiber member 15 closer to the calibration spectrometer 23, to be capable of level-controlling the quantity of light when the quantity of light is changed by a known factor. A comparison operation part 24 processes data from the spectrometers 22 and 23 and outputs the processed data to a control part of the semiconductor treater. This method is now specifically described.

Figure 6:
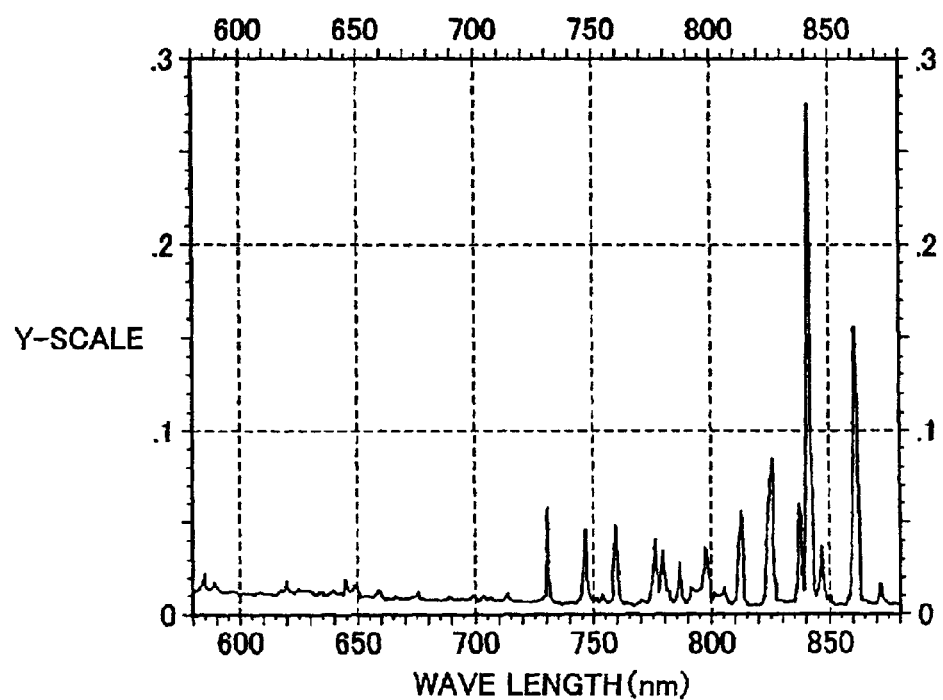
FIG. 6 illustrates a waveform in an analytical spectrometer.
Figure 7:
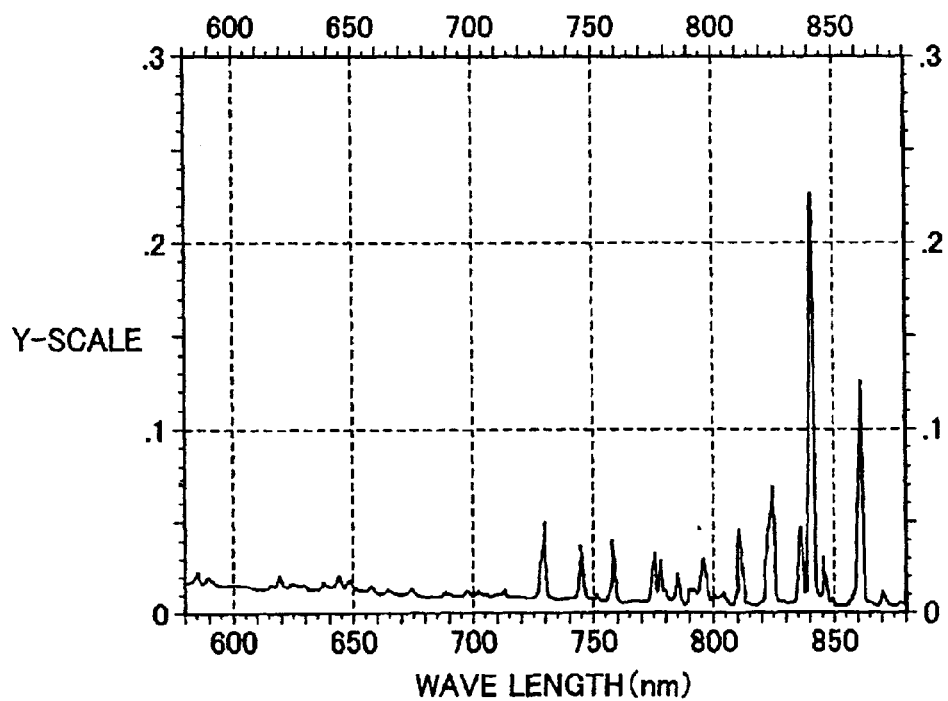
FIG. 7 illustrates a waveform in a calibration spectrometer.

FIG. 6 shows data obtained by performing spectroscopy on light emitted from the analyzing discharge part 10 mounted on a dry etching apparatus by the analytical spectrometer 22. FIG. 7 shows data obtained by performing spectroscopy on light emitted from the calibration discharge part 14 by the calibration spectrometer 23. An emission spectrum of chlorine radicals is mainly observed between wavelengths 730 nm and 870 nm in each of FIGS. 6 and 7.

The calibration discharge part 14 is filled with a gas mixture of $BCl_3$ (boron trichloride)/$Cl_2$ (chlorine)=20 sccm/ 80 sccm under a pressure of not more than 15 mTorr.

As to the light emitted from the analyzing discharge part 10 mounted on the dry etching apparatus shown in FIG. 6, it is understood that the emission strength of chlorine radicals is higher than that shown in FIG. 7. While this example is executed under a high chlorine partial pressure condition ($BCl_3/Cl_2$=10 sccm/90 sccm under equivalent pressure), representative wavelengths (725 nm, 741 nm, 755 nm, 772 nm, 775 nm, 833 nm etc.) of chlorine radicals have high strength and it is readily determinable that the partial pressure of chlorine is large.

As understood from this embodiment, change of the gas stored in the treater can be sensed by comparing the wavelengths, the strength levels or the shapes of the emission spectra from plasmas in the analytical discharge part 10 and the calibration discharge part 14 with each other when the calibration discharge part 14 is filled with gas having prescribed treatment conditions for the treater to be subjected to gas analysis.

For example, the wavelength and the strength of the emission spectrum of the gas filling the calibration discharge part 14 are previously input in the comparison operation part 24 from the treater, to be compared with the wavelength and the strength of the emission spectrum from the plasma of the analytical discharge part 10. If the wavelengths are identical to each other, the strength levels are compared with each other for determining whether or not the same are within a previously set range. If the wavelengths are different from each other, an error is posted to the treater while candidates for elements corresponding to the wavelengths can be shown from a database of emission spectra.

The wavelengths of the emission spectra are selected by providing a threshold for the emission strength. Only signals having strength levels exceeding the threshold are recognized as wavelengths. Thus, the threshold can be matched with a measuring system for enabling stable measurement also when a large quantity of noise results from stray light or the like.

No treatment plasma of the semiconductor treater is employed for this evaluation. Therefore, comparative analysis can be made in situ also when the semiconductor treater is in operation. Also when the flow rate, the type or the pressure of the gas is changed by some cause, this abnormality can be readily sensed.

Third Embodiment

A third embodiment of the present invention is now described with reference to a method of detecting atmospheric leakage, frequently causing a problem in an apparatus employing a vacuum.

Large atmospheric leakage can be sensed by monitoring a vacuum meter provided on the apparatus. However, it is difficult to sense small leakage through change of the degree of vacuum, which generally exhibits no change particularly when a vacuum pump is in operation.

According to this embodiment, the emission spectrum of the plasma 2 in the gas analytical discharge part 5 shown in FIG. 1 is checked. Atmospheric leakage can be readily and precisely sensed by checking presence/absence of emission spectra of atmosphere forming components such as nitrogen ($N_2$: 835 nm, 326 nm, 331 nm, 880 nm, 891 nm, 428 nm, 576 nm, 580 nm, 833 nm, 662 nm, 871 nm, 888 nm, 727 nm and 790 nm), oxygen (O: 437 nm, 502 nm, 533 nm, 544 nm, 505 nm, 616 nm, 648 nm, 700 nm, 725 nm and 777 nm), water (OH: 507 m), argon (Ar: 451 nm, 485 nm, 550 nm, 603 nm, 697 nm, 707 nm, 750 nm and 415 nm), carbon dioxide (CO: 484 nm, 313 nm, 283 nm, 239 nm, 245 nm, 249 nm, 271 nm, 349 nm, 370 nm, 451 nm, 520 nm, 551 nm, 606 nm and 662 nm, $CO_2$: 288 nm, 290 nm and 337 nm) etc. and hydrogen (H: 434 nm, 488 nm and 656 nm) resulting from water dissociated in the plasma.

According to this method, no plasma employed for treatment in the semiconductor treater is utilized. Therefore, the aforementioned spectra will not overlap with the spectrum of treatment gas but the emission spectra of the aforementioned atmospheric components can be readily satisfactorily sensed and leakage can be tested at arbitrary timing.

When the calibration discharge part 14 shown in FIG. 4 is filled with a specific quantity of atmosphere as standard treatment gas of the semiconductor treater and an emission spectrum thereof is compared with that of the analytical discharge part 10, atmospheric leakage can be more readily checked during treatment.

The calibration discharge part 14 may be filled with specific gas (in a single or mixed state) regardless of the atmospheric leakage. Also when data of the emission spectrum of the specific gas is unknown and general emission spectroscopic inspection is unavailable, inspection of inclusion or evaluation of the specific gas can be readily performed by comparing emission spectra. Also when gas having a known emission spectrum is employed depending on the mixed gas or discharge conditions and the strength of the spectrum is changed or the spectrum overlaps with that of another gas to cause difficulty in identification of the gas species, inspection of inclusion or evaluation of the mixed gas can be readily performed by comparing the pattern of the emission spectrum in the calibration discharge part 14 with the known emission spectrum of the gas.

In each of the aforementioned first to third embodiments, atmospheric leakage or abnormality of gas conditions can be sensed before treating a product by performing the in-situ gas analysis before product treatment in the semiconductor treater or before starting to feed gas, i.e., before generating a plasma. Thus, no product treatment is required and the yield is not reduced.

While the discharge parts 5, 10 and 14 are made of quartz in the first to third embodiments, another material may be employed so far as the same is dielectric and transparent to a measured wavelength region. When the gas to be analyzed contains fluorine, sapphire (single-crystalline alumina), for example, may be employed since fluorine reacts with quartz.

According to the present invention, as hereinabove described, no plasma in product treatment is employed and hence the inventive method is applicable to gas analysis of a non-plasma apparatus. Further, an electrodeless plasma is employed, to cause no metal contamination. In addition, precise in-situ gas analysis is enabled by emission comparison with calibration gas.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A gas analyzing method for a semiconductor treater comprising steps of:
   taking out gas to be analyzed from a chamber of said semiconductor treater;
   storing said gas to be analyzed in a gas analytic chamber;
   feeding a high frequency into said gas analytic chamber from outside said gas analytic chamber for forming a plasma in said gas analytic chamber; and
   analyzing the emission spectrum of said plasma.

2. The gas analyzing method for a semiconductor treater according to claim 1, performing said analysis in situ without stopping said semiconductor treater.

3. The gas analyzing method for a semiconductor treater according to claim 1, performing said analysis before product treatment in said semiconductor treater.

4. The gas analyzing method for a semiconductor treater according to claim 1, further comprising steps of:
   preparing a calibration plasma generation chamber independently of said gas analytic chamber and filling up said calibration plasma generation chamber with known gas, and
   generating a plasma of said known gas in said calibration plasma generation chamber,
   for comparing the emission spectrum of said plasma of said gas to be analyzed with the emission spectrum of said plasma of said known gas and analyzing said gas to be analyzed.

5. The gas analyzing method for a semiconductor treater according to claim 4, wherein
   said known gas contains molecules or atoms forming the atmosphere.

6. The gas analyzing method for a semiconductor treater according to claim 4, introducing specific gas having no emission spectrum data and allowing no general emission spectral analysis as said known gas,
   for comparing the emission spectrum of said plasma of said gas to be analyzed with the emission spectrum of a plasma of said specific gas thereby checking inclusion of said specific gas in said chamber of said semiconductor treater.

* * * * *